United States Patent
Serego Allighieri et al.

(10) Patent No.: US 6,841,090 B1
(45) Date of Patent: Jan. 11, 2005

(54) DISINFECTING COMPOSITION AND PROCESS FOR DISINFECTING SURFACES

(75) Inventors: Giadro Serego Allighieri, Rome (IT); Giuseppe Sirianni, Catanzaro (IT); Vincenzo Tomarchio, Alcamo (TP) (IT); Marina Trani, London (GB)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 09/647,832

(22) PCT Filed: Apr. 7, 1999

(86) PCT No.: PCT/IB99/00602

§ 371 (c)(1),
(2), (4) Date: Oct. 5, 2000

(87) PCT Pub. No.: WO99/52360

PCT Pub. Date: Oct. 21, 1999

(30) Foreign Application Priority Data

Apr. 8, 1998 (EP) .............................................. 98870074

(51) Int. Cl.[7] .................................................. C09K 3/00
(52) U.S. Cl. .............................. 252/186.1; 252/186.42; 252/186.43; 510/370; 510/372; 510/375; 510/378
(58) Field of Search ........................ 252/186.6, 186.42, 252/186.43, 186.1; 510/370, 372, 375, 378

(56) References Cited

U.S. PATENT DOCUMENTS

| | | | | |
|---|---|---|---|---|
| 4,347,149 A | * | 8/1982 | Smith et al. ................... | 8/137 |
| 4,430,236 A | * | 2/1984 | Franks ........................ | 510/303 |
| H269 H | * | 5/1987 | Malik .......................... | 422/37 |
| 5,075,026 A | * | 12/1991 | Loth et al. ................... | 510/101 |
| 5,382,376 A | * | 1/1995 | Michael et al. ............. | 510/413 |
| 5,393,468 A | * | 2/1995 | Erilli et al. ................. | 510/417 |
| 5,403,587 A | * | 4/1995 | McCue et al. .............. | 424/736 |
| 5,545,374 A | * | 8/1996 | French et al. ................. | 422/28 |
| 5,620,655 A | * | 4/1997 | Nevermann .................. | 422/28 |

FOREIGN PATENT DOCUMENTS

| | | |
|---|---|---|
| DE | 196 36 114 A1 | 3/1998 |
| GB | 2 298 791 | 9/1996 |
| WO | WO 94 17661 | 8/1994 |
| WO | WO 97 25106 | 7/1997 |
| WO | WO 97 31093 | 8/1997 |
| WO | WO 97-42276 | * 11/1997 |

* cited by examiner

Primary Examiner—Cephia D. Toomer
(74) Attorney, Agent, or Firm—Kevin L. Waugh; Jason J. Camp; Steven W. Miller

(57) ABSTRACT

Liquid disinfecting compositions comprise an effective amount of a disinfecting material and a poly (alkylene glycol) ether having the following formula: $R_1$—O—$(CH_2$—$CHR_2O)_n$—$R_3$, wherein $R_1$ and $R_2$ are each independently hydrogen or a substituted or unsubstituted, saturated or unsaturated, linear or branched hydrocarbon chain having from 1 to 30 carbon atoms or a hydroxy bearing linear or branched hydrocarbon chain having from 1 to 30 carbon atoms. $R_3$ is a substituted or unsubstituted, saturated, or unsaturated, linear or branched hydrocarbon chain having from 1 to 30 carbon atoms or a hydroxy bearing linear or branched hydrocarbon chain having from 1 to 30 carbon atoms, and n is greater than 2. Processes of disinfecting and hard-surface employ such a composition.

24 Claims, No Drawings

DISINFECTING COMPOSITION AND PROCESS FOR DISINFECTING SURFACES

TECHNICAL FIELD

The present invention relates to disinfecting compositions which can be used to disinfect various surfaces including inanimate surfaces such as hard surfaces like walls, tiles, floors, countertops, tables, glass, bathroom surfaces, kitchen surfaces. Advantageously the present compositions also deliver excellent cleaning performance and excellent shine.

BACKGROUND

Antimicrobial compositions contain materials which have the ability to disinfect. It is generally recognised that a disinfecting material greatly reduces or even eliminates the micro-organisms existing on a surface.

Although disinfecting compositions based on known disinfecting materials like bleach, quaternary ammonium compound, essential oil or the like, provide good immediate disinfecting properties, they do not maintain the disinfecting activity of the compositions for prolonged periods after their application to a hard-surface, to disinfect. Also consumers are looking for disinfecting compositions that on top of the disinfecting properties also provide excellent cleaning performance, especially on greasy soils while not leaving visible streak/filming on the surface upon drying.

It is thus an object of the present to provide not only effective disinfecting performance of any treated surface, with maximum efficiency, but also a greatly prolonged disinfecting action after application. Another object of the present invention is to provide compositions delivering on top of immediate and long lasting disinfecting properties, also excellent cleaning performance while further improving the shine onto the surface treated.

It has now been found that this can be achieved by formulating a liquid composition comprising an effective amount of disinfecting material and a poly(alkylene glycol) alkyl ether as defined herein. In a preferred embodiment the disinfecting material is a peroxygen bleach and/or an antimicrobial essential oil and/or an active thereof. Thus compositions are provided which encounter good acceptance amongst the consumers who are looking for disinfecting compositions based on safer and natural compounds.

Advantageously, effective immediate disinfecting performance as well as long lasting disinfecting performance is provided using a low total level of disinfecting materials.

Indeed, the present invention is based on the finding that by adding a single ingredient, i.e. the poly(alkylene glycol) alkyl ether as defined herein, to a composition comprising a disinfecting material, not only excellent immediate disinfecting performance but also improved long lasting disinfecting performance is provided, on top of excellent cleaning properties, especially on greasy stains, and excellent shine properties. Advantageously, the present invention allows the formulation of cost effective compositions.

An advantage of the present compositions is that they may be used to provide effective immediate and long lasting disinfection on any surfaces, even at high dilution levels, i.e., up to dilution levels of from 1:100 (composition:water).

Another advantage of the present invention is that immediate and long lasting disinfection is provided on a broad range of pure bacterial strains including Gram positive and Gram negative bacterial strains. The combination of peroxygen bleach and an antimicrobial essential oil or active thereof as the disinfecting material, according to the present invention is particularly effective on Gram negative bacterial strains.

SUMMARY OF THE INVENTION

The present invention encompasses a liquid disinfecting composition comprising an effective amount of a disinfecting material and a poly(alkylene glycol) alkyl ether as defined herein after. In a preferred embodiment the disinfecting material is a peroxygen bleach and/or an antimicrobial essential oil and/or an active thereof.

The present invention further encompasses a process for disinfecting a hard- surface wherein a liquid composition according to the present invention, is applied onto said surface.

The present invention also encompasses a liquid disinfecting composition as defined herein, packaged in a spray dispenser, as well as a wipe impregnated with a liquid disinfecting composition as defined herein.

DETAILED DESCRIPTION OF THE INVENTION

The Compositions:

The Disinfecting Material

An essential ingredient of the present invention is an effective amount of a disinfecting material or a mixture thereof.

By "disinfecting material", it is meant herein any known ingredient having the ability of reducing or even eliminating by killing the microorganisms existing on a surface.

By "an effective amount of a disinfecting material", it is meant herein an amount sufficient to allow the disinfecting material to perform its action, i.e. to reduce the number of micro-organisms existing on a given surface. Depending on the disinfecting material used the amount used may be different. Typically, the compositions of the present invention comprise from 0.001% to 40% by weight of the total composition of a disinfecting material, preferably from 0.05% to 10% and more preferably from 0.1% to 5%.

Suitable disinfecting materials are all those known by those skilled in the art for the purpose of disinfecting and may include bleaches like peroxygen bleaches and/or chlorine-type bleaches, antimicrobial essential oils or actives thereof, quaternary ammonium compounds, phenolic compounds, aldehydes like glutaraldehyde, formaldehyde, glyoxal, parabens like ethyl paraben, propyl paraben, methyl paraben, organic acids and peroxy acids, alcohols and mixtures thereof.

Preferred disinfecting materials for use herein include a peroxygen bleach, or an antimicrobial essential oil, or an active thereof, or a mixture of a peroxygen bleach and such an antimicrobial essential oil or an active thereof.

A preferred disinfecting material for use herein is a peroxygen bleach or a mixture thereof. Preferred peroxygen bleach is hydrogen peroxide, or a water soluble source thereof, or mixtures thereof. Hydrogen peroxide is most preferred to be used herein.

The presence of the peroxygen bleach, especially hydrogen peroxide, in the compositions according to the present invention contribute to the disinfection properties of said compositions. Indeed, said peroxygen bleach may attack the vital function of the micro-organism cells, for example, it may inhibit the assembling of ribosomes units within the cytoplasm of the micro-organisms cells. Also the peroxygen bleach, like hydrogen peroxide, is an oxidiser that generates hydroxyl free radicals which attack proteins and nucleic acids. Furthermore, the presence of the peroxygen bleach, especially hydrogen peroxide, provides good stain removal benefits when used in any hard surface application.

As used herein a hydrogen peroxide source refers to any compound which produces hydrogen peroxide when said compound is in contact with water. Suitable water-soluble sources of hydrogen peroxide for use herein include percarbonates, persilicates, persulphates such as monopersulfate, perborates and peroxyacids such as diperoxydodecandioic acid (DPDA), magnesium perphthalic acid and mixtures thereof.

In addition, other classes of peroxides can be used as an alternative to hydrogen peroxide and sources thereof or in combination with hydrogen peroxide and sources thereof. Suitable classes include dialkylperoxides, diacylperoxides, preformed percarboxylic acids, organic and inorganic peroxides and/or hydroperoxides.

Typically, peroxygen bleach or a mixture thereof is present in the compositions according to the present invention at a level up to 20% by weight of the total composition, preferably from 0.1% to 15%, and more preferably from 0.5% to 10%.

Another particularly preferred disinfecting material for use herein is an antimicrobial essential oil or an active thereof, or a mixture thereof.

Suitable antimicrobial essential oils for use herein are those essential oils which exhibit antimicrobial activity. By "actives of essential oils", it is meant herein any ingredient of essential oils that exhibit antimicrobial activity. It is speculated that said antimicrobial essential oils and actives thereof act as proteins denaturing agents.

Such antimicrobial essential oils include, but are not limited to, those obtained from thyme, lemongrass, citrus, lemons, orange, anise, clove, aniseed, pine, cinnamon, geranium, roses, mint, lavender, citronella, eucalyptus, peppermint, camphor, ajowan, sandalwood, rosmarin, vervain, fleagrass, lemongrass, ratanhiae, cedar and mixtures thereof. Preferred antimicrobial essential oils to be used herein are thyme oil, clove oil, cinnamon oil, geranium oil, eucalyptus oil, peppermint oil, citronella oil, ajowan oil, mint oil or mixtures thereof.

Actives of essential oils to be used herein include, but are not limited to, thymol (present for example in thyme, ajowan), eugenol (present for example in cinnamon and clove), menthol (present for example in mint), geraniol (present for example in geranium and rose, citronella), verbenone (present for example in vervain), eucalyptol and pinocarvone (present in eucalyptus), cedrol (present for example in cedar), anethol (present for example in anise), carvacrol, hinokitiol, berberine, ferulic acid, cinnamic acid, methyl salicylic acid, methyl salycilate, terpineol, limonene and mixtures thereof. Preferred actives of essential oils to be used herein are thymol, eugenol, verbenone, eucalyptol, terpineol, cinnamic acid, methyl salicylic acid, limonene, geraniol or mixtures thereof.

Thymol may be commercially available for example from Aldrich—Manheimer Inc, eugenol may be commercially available for example from Sigma, Systems—Bioindustries (SBI)—Manheimer Inc.

Typically, the antimicrobial essential oil or active thereof or mixture thereof is present in the composition at a level up to 20% by weight of the total composition, preferably at a level of at least 0.003% to 10%, more preferably from 0.006% to 10%, even more preferably from 0.01% to 8% and most preferably from 0.03% to 3%.

A highly preferred embodiment of the compositions herein combines said antimicrobial essential oil or an active thereof or a mixture thereof with a peroxygen bleach.

Suitable quaternary ammonium compounds for use herein are quaternary ammonium compounds containing alkyl or substituted alkyl groups, alkyl amide and carboxylic acid groups, ether groups, unsaturated alkyl groups, and cyclic quaternary ammonium compounds, which can be chlorides, dichlorides, bromides, methylsulphates, chlorophenates, cylcohexylsulphamates or salts of the other acids. Among the possible cyclic quaternary ammonium compounds are the following:

alkylpyridinium chlorides and/or sulphates, the alkyl group being preferably cetyl, dodecyl or hexadecyl group;

alkylisoquinolyl chlorides and/or bromides, the alkyl group being preferably dodecyl group. Particularly suitable quaternary ammonium compounds for use herein include alkyl dimethyl benzyl ammonium chloride, octyl decyl dimethyl ammonium chloride, dioctyl dimethyl ammonium chloride, didecyl dimethyl ammonium chloride, alkyl dimethyl ammonium saccharinate, cetylpyridinium and mixtures thereof.

Suitable phenolic compounds for use herein include o-penyl-phenol, o-benzyl(p-chlorophenol), 4-tertamylphenol and mixtures thereof.

Other suitable disinfecting materials for use herein include chlorine-type bleaches like hypochlorite.

Effective disinfecting performance is obtained with the compositions according to the present inventions on a variety of micro-organisms including Gram negative bacteria like *Pseudomonas aeroginosa, Escherichia coli, Salmonella* as well as on Gram positive bacteria like *Enterococcus hirae, Staphylococcus aureus*, present on infected surfaces, even if used in highly diluted conditions, e.g. up to a dilution level of 1:100 (composition:water).

The disinfecting properties of a composition according to the present invention may be measured by the bactericidal activity of said composition. A test method suitable to evaluate the bactericidal activity of a composition on infected surfaces is described in European Standard, prEN 1040, CEN/TC 216 N 78, dated November 1995 issued by the European committee for standardisation, Brussels. European Standard, prEN 1040, CEN/TC 216 N 78, specifies a test method and requirements for the minimum bactericidal activity of a disinfecting composition. The test is passed if the bacterical colonies forming units (cfu) are reduced from a $10^7$ cfu (initial level) to a $10^2$ cfu (final level after contact with the disinfecting product), i.e. a $10^5$ reduction of the viability is necessary. The compositions according to the present invention pass this test, even if used in highly diluted conditions. Other suitable methods are the AOAC Usedilution method, AOAC Germicidal Spray method, AOAC Wipes method (US) and AFNOR T72-190 (Europe).

The poly(alkylene glycol) alkyl ether

Another essential ingredient of the present invention is a poly(alkylene glycol) alkyl ether, as defined herein after, or a mixture thereof.

Typically, the composition of the present invention comprises from 0.001% to 10% by weight of the total composition of such a poly(alkylene glycol) alkyl ether or a mixture thereof, preferably from 0.005% to 2%, more preferably from 0.01% to 1%, even more preferably from 0.05% to 0.5% and most preferably from 0.08% to 0.4%.

Suitable poly(alkylene glycol) alkyl ethers for use herein are according the following formula:

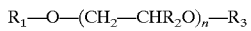

$R_1-O-(CH_2-CHR_2O)_n-R_3$ wherein $R_1$ and $R_2$ each independently are hydrogen or a substituted or unsubstituted, saturated or unsaturated, linear or branched hydrocarbon chain having from 1 to 30 carbon atoms or a hydroxy bearing linear or branched hydrocarbon chain having from 1 to 30 carbon atoms, $R_3$ is a substituted or unsubstituted, saturated or unsaturated, linear or branched hydrocarbon chain having from 1 to 30 carbon atoms or a hydroxy bearing linear or branched hydrocarbon chain having from 1 to 30 carbon atoms, n is a number greater than 2, or a mixture thereof.

Preferably $R_1$ and $R_2$ each independently are hydrogen, or a substituted or unsubstituted, linear or branched, alkyl group or alkenyl group having from 1 to 30 carbon atoms, preferably from 1 to 16 carbon atoms, more preferably from 1 to 8 and most preferably from 1 to 4, or a hydroxy bearing linear or branched alkyl or alkenyl group having from 1 to 30 carbon atoms, more preferably from 1 to 16, even more preferably from 1 to 4, and most preferably $R_1$ and $R_2$ are methyl or hydrogen.

Preferably $R_3$ is a substituted or unsubstituted, linear or branched, alkyl group or alkenyl group having from 1 to 30 carbon atoms, preferably from 1 to 16 carbon atoms, more preferably from 1 to 8 and most preferably from 1 to 4, or a substituted or unsubstituted, saturated or unsaturated, linear or branched aryl group having up to 30 carbon atoms, preferably from 3 to 16 and more preferably from 4 to 8 carbon atoms, or a hydroxy bearing linear or branched alkyl or alkenyl group having from 1 to 30 carbon atoms, more preferably from 1 to 16 even more preferably from 1 to 8, and most preferably $R_3$ is butyl.

Preferably n is a number of at least 3, preferably from 3 to 2300, more preferably 3 to 100, more preferably from 3 to 20 and most preferably from 3 to 10.

The poly(alkylene glycol) alkyl ethers for use herein preferably have an average molecular weight from 164 to 100 000, more preferably from 180 to 10 000 and most preferably from 200 to 1 000.

Suitable poly(alkylene glycol) alkyl ethers for use herein include poly(propylene glycol) mono butyl ether, poly(ethylene glycol-co-propylene glycol) mono butyl ether, poly(ethylene glycol) dimethyl ether, poly(ethylene glycol-co-propylene glycol) dimethyl ether, poly(ethylene glycol) stearate or mixtures thereof.

Poly(propylene glycol) mono butyl ether (average molecular weight 340) is commercially available from Aldrich or from Union Carbide under Ucon-lb 65®.

The present invention is based on the finding that the addition of poly(alkylene glycol) alkyl ether as defined herein, in a liquid composition comprising a disinfecting material delivers excellent immediate disinfecting performance and improves the long lasting disinfecting performance of said composition. Thus, an advantage of the present invention is to get effective immediate and long lasting disinfecting performance with low total level of disinfecting materials.

Indeed, it is speculated that the presence of poly(alkylene glycol) alkyl ether in the disinfecting compositions of the present invention promotes the formation of an hydrophilic layer that is left behind upon drying after having applied the compositions onto a hard-surface. The formation of such a layer on the surface of the hard-surface treated with the disinfecting compositions herein allows a more uniform distribution of the disinfecting material. This results in better availability of the disinfecting material for immediate and long lasting disinfecting performance. In other words, the compositions of the present invention allows to reduce or even eliminate the contamination of micro-organisms over time, typically up to 24 hours after the surface has been treated with said composition.

It has further been found that optimum immediate and long lasting disinfecting performance is obtained when the poly(alkylene glycol) alkyl ether, as defined herein, is added in the composition on top of a peroxygen bleach, preferably hydrogen peroxide, together with an antimicrobial essential oil or active thereof, as the disinfecting material.

Advantageously, the immediate and long lasting disinfection benefits are obtained with the compositions of the present invention even when used under highly diluted conditions, i.e., up to dilution levels of from 1:100 (composition:water).

Long lasting disinfection properties of the compositions herein may be measured by the bactericidal activity of said compositions. A test method suitable to evaluate the long lasting bactericidal activity of a composition may be as follow: First, the surfaces (e.g. glass) to be tested are respectively treated with either a composition according to the present invention or a reference composition, e.g., a negative control composed of pure water (for example by spraying the composition directly on the surface or first spraying the composition on a sponge used to clean the surface or when the composition herein is executed in the form of wipe by wiping the surface therewith). After a variable time frame (e.g. 24 hours) each surface is respectively inoculated with bacteria ($10^{5-7}$ cfu/slide) cultured in for example TSB (Tryptone Soya Broth) and left typically from a few seconds to 2 hours before evaluating the remaining living bacteria. Then living bacteria (if any) are recovered from the surface (by re-suspending the bacteria into the neutralisation broth and plating them on agar) and incubated at appropriate temperature, e.g. 37° C. to let them grow typically over night. Finally, an evaluation of the residual antibacterial efficacy of the composition is made by comparing side by side the cultures and/or dilutions thereof (e.g. $10^{-2}$ or $10^{-1}$) resulting from the surfaces treated with the compositions according to the present invention and the reference composition.

The addition of the poly(alkylene glycol) alkyl ether as defined herein, in the liquid disinfecting compositions of the present invention provide improved cleaning performance, especially on greasy stains, when used to treat hard-surfaces. Furthermore, the hydrophilic layer left behind when treating a hard-surface with a composition of the present invention comprising the disinfecting material and the poly(alkylene glycol) alkyl ether as defined herein, has the ability to attract and retain ambient atmospheric water vapour thereby reducing the adhesion of soils on the surface once treated and/or facilitating removal of soils subsequently deposited thereon, i.e. less work (e.g. less scrubbing and/or wiping and/or less chemical action) is required to remove the soils in the next-time disinfecting/cleaning operation.

The hydrophilic layer left behind when treating a hard-surface with a composition of the present invention leaves the water coming in contact with the surface having first been treated with the composition herein (e.g. water which is used to rinse off the surface having been so treated) uniformly spread over the surface ("sheeting effect") instead of forming droplets. This way the formation of watermarks upon drying is reduced or even eliminated. This results in improved surface shine. Also reduced filming and streaking is observed due to the presence of the poly(alkylene glycol)

alkyl ether as defined herein in the disinfecting compositions of the present invention. This further results in improved surface shine.

Furthermore, the hydrophilic layer so formed due to the presence of the poly(alkylene glycol) alkyl ether has the ability to remain on the surface even after several cycles of rinsing (e.g., when water comes onto the surface later on for example in a sink during daily household operation), thus providing long lasting protection against the formation of watermarks, hence, long lasting shiny surfaces.

Typically, the liquid compositions of the present invention have a pH as is of not more than 12.0, more preferably from 1 to 10, and most preferably from 2 to 9. The pH of the compositions can be adjusted by using organic or inorganic acids, or alkalinising agents.

Optional Ingredients

Surfactants

The compositions according to the present invention may further comprise a surfactant or mixtures thereof. Suitable surfactants to be used herein may be any surfactant known to those skilled in the art including anionic, nonionic, cationic, amphoteric and/or zwitterionic surfactants. Surfactants contribute to the cleaning performance of the disinfecting compositions of the present invention.

Particularly suitable anionic surfactants to be used herein include water soluble salts or acids of the formula $ROSO_3M$ wherein R is preferably a $C_6-C_{24}$ hydrocarbyl, preferably an alkyl or hydroxyalkyl having a $C_{10}-C_{20}$ alkyl component, more preferably a $C_{12}-C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyl-diphenyl-ether-sulphonates and alkylcarboxylates. Other anionic surfactants can include salts (including, for example, sodium, potassium, ammonium, and substituted ammonium salts such as mono-, di- and triethanolamine salts) of soap, $C_9-C_{20}$ linear alkylbenzenesulfonates, $C_8-C_{22}$ primary or secondary alkanesulfonates, $C_8-C_{24}$ olefinsulfonates, sulfonated polycarboxylic acids prepared by sulfonation of the pyrolyzed product of alkaline earth metal citrates, e.g., as described in British patent specification No. 1,082,179, $C_8-C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}-C_{18}$ monoesters) diesters of sulfosuccinate (especially saturated and unsaturated $C_6-C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO-M^+$ wherein R is a $C_8-C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred anionic surfactants for use in the compositions herein are the alkyl benzene sulfonates, alkyl sulfates, alkyl alkoxylated sulfates, paraffin sulfonates and mixtures thereof.

Suitable amphoteric surfactants to be used herein include amine oxides having the following formula $R_1R_2R_3NO$ wherein each of R1, R2 and R3 is independently a saturated substituted or unsubstituted, linear or branched hydrocarbon chains of from 1 to 30 carbon atoms. Preferred amine oxide surfactants to be used according to the present invention are amine oxides having the following formula $R_1R_2R_3NO$ wherein R1 is an hydrocarbon chain comprising from 1 to 30 carbon atoms, preferably from 6 to 20, more preferably from 8 to 16, most preferably from 8 to 12, and wherein R2 and R3 are independently substituted or unsubstituted, linear or branched hydrocarbon chains comprising from 1 to 4 carbon atoms, preferably from 1 to 3 carbon atoms, and more preferably are methyl groups. R1 may be a saturated substituted or unsubstituted, linear or branched hydrocarbon chain.

Suitable amine oxides for use herein are for instance natural blend $C_8-C_{10}$ amine oxides as well as C12–C16 amine oxides commercially available from Hoechst.

Suitable zwitterionic surfactants to be used herein contain both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylates and sulfonates, although other groups like sulfates, phosphonates, and the like can be used. A generic formula for some zwitterionic surfactants to be used herein is

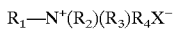

$$R_1-N^+(R_2)(R_3)R_4X^-$$

wherein $R_1$ is a hydrophobic group; $R_2$ and $R_3$ are each $C_1-C_4$ alkyl, hydroxy alkyl or other substituted alkyl group which can also be joined to form ring structures with the N; $R_4$ is a moiety joining the cationic nitrogen atom to the hydrophilic group and is typically an alkylene, hydroxy alkylene, or polyalkoxy group containing from 1 to 10 carbon atoms; and X is the hydrophilic group which is preferably a carboxylate or sulfonate group. Preferred hydrophobic groups $R_1$ are alkyl groups containing from 1 to 24, preferably less than 18, more preferably less than 16 carbon atoms. The hydrophobic group can contain unsaturation and/or substituents and/or linking groups such as aryl groups, amido groups, ester groups and the like. In general, the simple alkyl groups are preferred for cost and stability reasons.

Highly preferred zwitterionic surfactants include betaine and sulphobetaine surfactants, derivatives thereof or mixtures thereof. Said betaine or sulphobetaine surfactants are preferred herein as, they help disinfection by increasing the permeability of the bacterial cell wall, thus allowing other active ingredients to enter the cell.

Furthermore, due to the mild action profile of said betaine or sulphobetaine surfactants, they are particularly suitable for the cleaning of delicate surfaces, e.g., surfaces in contact with food and/or babies. Betaine and sulphobetaine surfactants are also extremely mild to the skin and/or surfaces to be treated.

Suitable betaine and sulphobetaine surfactants to be used herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference. Preferred betaine and sulphobetaine surfactants herein are according to the formula:

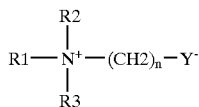

wherein R1 is a hydrocarbon chain containing from 1 to 24 carbon atoms, preferably from 8 to 18, more preferably from 12 to 14, wherein R2 and R3 are hydrocarbon chains containing from 1 to 3 carbon atoms, preferably 1 carbon atom, wherein n is an integer from 1 to 10, preferably from 1 to 6, more preferably is 1, Y is selected from the group consisting of carboxyl and sulfonyl radicals and wherein the sum of R1, R2 and R3 hydrocarbon chains is from 14 to 24 carbon atoms, or mixtures thereof.

Examples of particularly suitable betaine surfactants include $C_{12}$–$C_{18}$ alkyl dimethyl betaine such as coconutbetaine and $C_{10}$–$C_{16}$ alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

Other specific zwitterionic surfactants have the generic formulas:

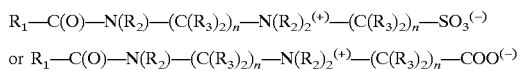

wherein each $R_1$ is a hydrocarbon, e.g. an alkyl group containing from 8 up to 20, preferably up to 18, more preferably up to 16 carbon atoms, each $R_2$ is either a hydrogen (when attached to the amido nitrogen), short chain alkyl or substituted alkyl containing from one to 4 carbon atoms, preferably groups selected from the group consisting of methyl, ethyl, propyl, hydroxy substituted ethyl or propyl and mixtures thereof, preferably methyl, each $R_3$ is selected from the group consisting of hydrogen and hydroxy groups and each n is a number from 1 to 4, preferably from 2 to 3, more preferably 3, with no more than one hydroxy group in any $(C(R_3)_2)$ moiety. The $R_1$ groups can be branched and/or unsaturated. The $R_2$ groups can also be connected to form ring structures. A surfactant of this type is a $C_{10}$–$C_{14}$ fatty acylamidopropylene(hydroxypropylene)sulfobetaine that is available from the Sherex Company under the trade name "Varion CAS sulfobetaine"®.

Suitable nonionic surfactants to be used herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Particularly suitable for use herein as nonionic surfactants are hydrophobic nonionic surfactants having an HLB (hydrophilic-lipophilic balance) below 16, preferably below 15, more preferably below 12, and most preferably below 10. Those hydrophobic nonionic surfactants have been found to provide good grease cutting properties.

Preferred hydrophobic nonionic surfactants to be used in the compositions according to the present invention are surfactants having an HLB below 16 and being according to the formula RO—$(C_2H_4O)_n(C_3H_6O)_m$H, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and, n and m are from 0.5 to 15, more preferably n+m is from 1 to 10 and, n and m are from 0 to 10. The preferred R chains for use herein are the C8 to $C_{22}$ alkyl chains. Accordingly, suitable hydrophobic nonionic surfactants for use herein are Dobanol $^R$ 91-2.5 (HLB=8.1; R is a mixture of C9 and $C_{11}$ alkyl chains, n is 2.5 and m is 0), or Lutensol $^R$ TO3 (HLB=8; R is a $C_{13}$ alkyl chains, n is 3 and m is 0), or Lutensol $^R$ AO3 (HLB=8; R is a mixture of $C_{13}$ and $C_{15}$ alkyl chains, n is 3 and m is 0), or Tergitol $^R$ 25L3 (HLB=7.7; R is in the range of $C_{12}$ to $C_{15}$ alkyl chain length, n is 3 and m is 0), or Dobanol $^R$ 23-3 (HLB=8.1; R is a mixture of $C_{12}$ and $C_{13}$ alkyl chains, n is 3 and m is 0), or Dobanol $^R$ 23-2 (HLB=6.2; R is a mixture of $C_{12}$ and $C_{13}$ alkyl chains, n is 2 and m is 0), or Dobanol $^R$ 45-7 (HLB=11.6; R is a mixture of $C_{14}$ and $C_{15}$ alkyl chains, n is 7 and m is 0) Dobanol $^R$ 23-6.5 (HLB=11.9; R is a mixture of $C_{12}$ and $C_{13}$ alkyl chains, n is 6.5 and m is 0), or Dobanol $^R$ 25-7 (HLB=12; R is a mixture of $C_{12}$ and $C_{15}$ alkyl chains, n is 7 and m is 0), or Dobanol $^R$ 91-5 (HLB=11.6; R is a mixture of $C_9$ and $C_{11}$ alkyl chains, n is 5 and m is 0), or Dobanol $^R$ 91-6 (HLB=12.5; R is a mixture of $C_9$ and $C_{11}$ alkyl chains, n is 6 and m is 0), or Dobanol $^R$ 91-8 (HLB=13.7; R is a mixture of $C_9$ and $C_{11}$ alkyl chains, n is 8 and m is 0), Dobanol $^R$ 91-10 (HLB=14.2; R is a mixture of $C_9$ to $C_{11}$ alkyl chains, n is 10 and m is 0), or mixtures thereof. Preferred herein are Dobanol $^R$ 91-2.5, or Lutensol $^R$ TO3, or Lutensol $^R$ AO3, or Tergitol $^R$ 25L3, or Dobanol $^R$ 23-3, or Dobanol $^R$ 23-2, or mixtures thereof. These Dobanol$^R$ surfactants are commercially available from SHELL. These Lutensol$^R$ surfactants are commercially available from BASF and these Tergitol$^R$ surfactants are commercially available from UNION CARBIDE.

Typically, the surfactant or mixtures thereof may be present in the composition of the present invention at a level of from 0.01% to 50% by weight of the total composition, preferably from 0.01% to 30% and more preferably from 0.05% to 20%.

Chelating Agents

The compositions herein may further comprise a chelating agent as a preferred optional ingredient. Suitable chelating agents may be any of those known to those skilled in the art such as the ones selected from the group comprising phosphonate chelating agents, amino carboxylate chelating agents or other carboxylate chelating agents, or polyfunctionally-substituted aromatic chelating agents or mixtures thereof.

Such phosphonate chelating agents may include etidronic acid (1-hydroxyethylidene-bisphosphonic acid or HEDP) as well as amino phosphonate compounds, including amino alkylene poly (alkylene phosphonate), alkali metal ethane 1-hydroxy diphosphonates, nitrilo trimethylene phosphonates, ethylene diamine tetra methylene phosphonates, and diethylene triamine penta methylene phosphonates. The phosphonate compounds may be present either in their acid form or as salts of different cations on some or all of their acid functionalities. Preferred phosphonate chelating agents to be used herein are diethylene triamine penta methylene phosphonates. Such phosphonate chelants are commercially available from Monsanto under the trade name DEQUESTO. Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy -3,5 isulfobenzene.

A preferred biodegradable chelating agent for use herein is ethylene diamine N,N'- disuccinic acid, or alkali metal, or alkaline earth, ammonium or substitutes ammonium salts thereof or mixtures thereof. Ethylenediamine N,N'- disuccinic acids, especially the (S,S) isomer have been extensively described in U.S. Pat. No. 4,704,233, Nov. 3, 1987 to Hartman and Perkins. Ethylenediamine N,N'-disuccinic acid is, for instance, commercially available under the tradename ssEDDS® from Palmer Research Laboratories.

Suitable amino carboxylate chelating agents useful herein include ethylene diamine tetra acetates, diethylene triamine pentaacetates, diethylene triamine pentoacetate (DTPA), N-hydroxyethylethylenediamine triacetates, nitrilotriacetates, ethylenediamine tetraproprionates, triethylenetetraaminehexa-acetates, ethanoldiglycines, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein include malonic acid, salicylic acid, glycine, aspartic acid, glutamic acid, or mixtures thereof.

Said chelating agents, especially phosphonate chelating agents like diethylene triamine penta methylene phosphonates, are particularly preferred in the compositions according to the present invention as they have been found to further contribute to the disinfecting properties of the compositions herein.

Typically, the compositions according to the present invention comprise up to 5% by weight of the total composition of a chelating agent, or mixtures thereof, preferably from 0.002% to 3% by weight and more preferably from 0.002% to 1.5%.

Radical Scavengers

The compositions herein may further comprise a radical scavenger as a preferred optional ingredient. Suitable radical scavengers for use herein include the well-known substituted mono and di hydroxy benzenes and derivatives thereof, alkyl- and aryl carboxylates and mixtures thereof. Preferred radical scavengers for use herein include di-tert-butyl hydroxy toluene, hydroquinone, di-tert-butyl hydroquinone, mono-tert-butyl hydroquinone, tert-butyl-hydroxy anysole, benzoic acid, toluic acid, catechol, t-butyl catechol, 2-methoxy-phenol, 2-ethoxy-phenol, 4-allyl-catechol, 2-methoxy-4-(2-propenyl)phenol, benzylamine, 1,1,3-tris(2-methyl-4-hydroxy-5-t-butylphenyl) butane, as well as n-propyl-gallate. Highly preferred for use herein is di-tert-butyl hydroxy toluene, which is for example commercially available from SHELL under the trade name IONOL CP®.

Typically, the compositions according to the present invention comprise up to 5% by weight of the total composition of a radical scavenger, or mixtures thereof, preferably from 0.01% to 1.5% by weight and more preferably from 0.01% to 1%.

Solvents

The compositions herein may comprise as an optional ingredient a solvent or mixtures thereof. When used, solvents will, advantageously, give an enhanced cleaning to the compositions of the present invention. Suitable solvents for incorporation in the compositions according to the present invention include propylene glycol derivatives such as n-butoxypropanol or n-butoxypropoxypropanol, water-soluble CARBITOL® solvents or water-soluble CELLOSOLVE® solvents. Water-soluble CARBITOL® solvents are compounds of the 2-(2-alkoxyethoxy)ethanol class wherein the alkoxy group is derived from ethyl, propyl or butyl. A preferred water-soluble carbitol is 2-(2-butoxyethoxy)ethanol also known as butyl carbitol. Water-soluble CELLOSOLVE® solvents are compounds of the 2-alkoxyethoxyethanol class, with 2-butoxyethoxyethanol being preferred. Other suitable solvents are benzyl alcohol, methanol, ethanol, isopropyl alcohol and diols such as 2ethyl-1,3-hexanediol and 2,2,4-trimethyl-1,3-pentanediol and mixture thereof. Preferred solvents for use herein are n-butoxypropoxypropanol, butyl carbitol® and mixtures thereof. A most preferred solvent for use herein is butyl carbitol®.

The solvents may typically be present within the compositions of the invention at a level up to 15% by weight, and preferably from 1% to 7% by weight of the composition.

pH Buffers

In the embodiment of the present invention wherein the compositions are formulated in the alkaline pH range, typically from 7 to 12, the compositions according to the present invention may further comprise a pH buffer or a mixture thereof, i.e. a system composed of a compound or a combination of compounds, whose pH changes only slightly when a strong acid or base is added.

Suitable pH buffers for use herein in neutral to basic condition include borate pH buffer, phosphonate, silicate and mixtures thereof. Suitable borate pH buffers for use herein include alkali metal salts of borates and alkyl borates and mixtures thereof. Suitable borate pH buffers to be used herein are alkali metal salts of borate, metaborate, tetraborate, octoborate, pentaborate, dodecaboron, borontrifluoride and/or alkyl borate containing from 1 to 12 carbon atoms, and preferably from 1 to 4. Suitable alkyl borate includes methyl borate, ethyl borate and propyl borate. Particularly preferred herein are the alkali metal salts of metaborate (e.g. sodium metaborate), tetraborate (e.g., sodium tetraborate decahydrate) or mixtures thereof.

Boron salts like sodium metaborate and sodium tetraborate are commercially available from Borax and Societa Chimica Larderello under the trade name sodium metaborate® and Borax®.

In the embodiment of the present invention wherein the compositions are formulated in the acidic pH range (i.e. below 7), preferably from 2 to 6, more preferably from 2 to 4, the compositions according to the present invention may further comprise a pH buffer or a mixture thereof, i.e. a system composed of a compound or a combination of compounds, whose pH changes only slightly when a strong acid or base is added.

Suitable pH buffers for use herein in acidic condition include organic acids and mixtures thereof. Suitable organic acids for use herein include monocarboxylic acids, dicarboxylic acids and tricarboxylic acids or mixtures thereof. Preferred organic acids for use herein include acetic acid, citric acid, malonic acid, maleic acid, malic acid, lactic acid, glutaric acid, glutamic acid, aspartic acid, methyl succinic acid, succinic acid or mixtures thereof. Particularly preferred herein are the citric acid and succinic acid or mixtures thereof.

Citric acid is commercially available as an aqueous solution from Jungbunzlauer under the trade name Citric acid®.

Typically, the compositions according to the present invention may comprise up to 15% by weight of the total composition of a pH buffer, or mixtures thereof, preferably from 0.01% to 10%, more preferably from 0.01% to 5% and most preferably from 0.1% to 3%.

The compositions herein may further comprise a variety of other optional ingredients such builders, stabilisers, bleach activators, soil suspenders, dye transfer agents, brighteners, perfumes, anti dusting agents, enzymes, dispersant, dye transfer inhibitors, pigments, perfumes and dyes.

Packaging Form of the Disinfecting Compositions

The compositions herein may be packaged in a variety of suitable detergent packaging known to those skilled in the art.

The disinfecting compositions herein in a liquid form may desirably be packaged in manually operated spray dispensing containers. Accordingly, the present invention also encompasses liquid compositions of the invention packaged in a spray dispenser, preferably in a trigger spray dispenser or in a pump spray dispenser.

For example, said spray-type dispensers allow to uniformly apply to a relatively large area of a surface to be disinfected the liquid compositions suitable for use according to the present invention; thereby contributing to the disinfecting properties of said compositions. Such spray-type dispensers are particularly suitable to disinfect vertical surfaces.

Suitable spray-type dispensers to be used according to the present invention include manually operated foam trigger-type dispensers sold for example by Specialty Packaging Products, Inc. or Continental Sprayers, Inc. These types of dispensers are disclosed, for instance, in U.S. Pat. No. 4,701,311 to Dunning et al. and U.S. Pat. No. 4,646,973 and U.S. Pat. No. 4,538,745 both to Focarracci. Particularly preferred to be used herein are spray-type dispensers such as T8500® or T8900® commercially available from Continental Sprayers International or T 8100® commercially available from Canyon, Northern Ireland. In such a dispenser the liquid composition is divided in fine liquid droplets resulting in a spray that is directed onto the surface to be treated. Indeed, in such a spray-type dispenser the composition contained in the body of said dispenser is directed through the spray-type dispenser head via energy communicated to a pumping mechanism by the user as said user activates said pumping mechanism. More particularly, in said spray-type dispenser head the composition is forced against an obstacle, e.g. a grid or a cone or the like, thereby providing shocks to help atomise the liquid composition, i.e. to help the formation of liquid droplets.

The compositions of the present invention may also be executed in the form of wipes. By "wipes", it is meant herein disposable towels incorporating a disinfecting composition according to the present invention. Preferably said wipes are packaged in a plastic box. Accordingly, the present invention also encompasses wipes, e.g., disposable towels, incorporating a composition as described herein before. Preferably said wipes are impregnated/wetted with a liquid disinfecting composition as described herein. The advantage of this execution is a faster usage of a disinfecting composition by the user, this even outside the house, i.e., there is no need for example to pour the liquid compositions according to the present invention on the surfaces to be disinfected and to dry it out with a cloth. In other words, wipes allow disinfecting of surfaces in one step.

Processes of Disinfecting a Hard-Surface

The present invention encompasses a process of disinfecting a hard-surface with a composition, as defined herein, said process comprising the step of applying said composition onto said surface.

The hard-surfaces to treat with the compositions herein are those typically found in houses like kitchens, bathrooms, e.g., tiles, walls, floors, chrome, glass, smooth vinyl, any plastic, plastified wood, table top, sinks, cooker tops, dishes, sanitary fittings such as sinks, showers, shower curtains, wash basins, WCs and the like. Hard-surfaces also include household appliances including, but not limited to, refrigerators, freezers, washing machines, automatic dryers, ovens, microwave ovens, dishwashers and so on.

In such a process a disinfecting composition, as described herein, needs to be contacted with the hard-surfaces to be disinfected. Thus, the present invention also encompasses a process of disinfecting a hard-surface with a disinfecting composition as described herein, wherein said process comprises the step of applying said composition to said hard-surface, preferably only infected portions thereof and optionally rinsing said hard-surface.

In the process of disinfecting hard-surfaces according to the present invention the disinfecting compositions as described herein are in liquid form and may be applied to the surface to be disinfected in their neat form or in their diluted form typically at a dilution level up to 100 times their weight of water, preferably into 80 to 2 times their weight of water, and more preferably 60 to 10 times.

In the preferred embodiment of the process of the present invention wherein said liquid composition is applied to a hard-surface to be disinfected in its diluted form, it is not necessary to rinse the surface after the composition has been applied, indeed no visible residues are left onto the surface.

The present invention will be further illustrated by the following examples.

Examples

The following compositions were made by mixing the listed ingredients in the listed proportions (weight % unless otherwise specified).

| Compositions (weight %) | I | II | III | IV | V | VI | VII |
|---|---|---|---|---|---|---|---|
| Hydrogen peroxide | 1.2 | 1.0 | 1.5 | 1.0 | 1.5 | 1.5 | 1.0 |
| Thymol | 0.045 | 0.02 | 0.1 | 0.01 | 0.02 | 0.02 | 0.02 |
| Geraniol | — | — | — | — | — | — | 0.03 |
| Poly(propylene glycol) mono butyl ether* | 0.25 | 0.25 | 0.5 | 0.5 | 0.5 | 0.5 | 0.25 |
| C10 Alkyl Sulphate | — | — | 7.0 | — | — | — | — |
| Benzyl alcohol | — | — | — | 0.8 | 0.8 | 0.8 | — |
| Amine oxide** | 0.55 | 0.40 | 0.9 | 0.9 | 0.9 | 0.9 | 0.4 |
| Butyl carbitol | 0.55 | 0.55 | — | 0.3 | 0.3 | 0.3 | 0.55 |
| Butoxy propanol | 0.55 | 0.55 | — | 1.2 | 1.2 | 1.2 | — |
| Propylene glycol butyl ether | — | — | — | — | — | — | 0.55 |
| Ethanol | 9.4 | 9.4 | 2.5 | 1.0 | 1.0 | 1.0 | 9.4 |
| Citric acid | 1.5 | 0.75 | 1.5 | 0.5 | — | 0.7 | 0.75 |
| Salicylic acid | 0.03 | 0.03 | 0.03 | 0.03 | 0.03 | 0.03 | 0.03 |
| Butyl hydroxy toluene | 0.01 | 0.01 | 0.01 | 0.01 | 0.01 | 0.01 | 0.01 |
| Water and minors | up to 100% | | | | | | |

Poly(propylene glycol) mono butyl ether* used herein has an average molecular weight of 340.
Amine oxide** is C12–C14 alkyl dimethyl amine oxide.

| Compositions (weight %) | VIII | IX | X | XI | XII | XIII |
|---|---|---|---|---|---|---|

| | | | | | | |
|---|---|---|---|---|---|---|
| Hydrogen peroxide | 1.2 | 1.0 | 1.0 | 1.0 | 1.5 | 1.5 |
| Thymol | 0.045 | 0.02 | 0.05 | 0.01 | 0.02 | 0.02 |
| Poly(ethylene glycol-co-propylene glycol)-mono butyl ether*** | 0.25 | 0.25 | 0.5 | 0.5 | 0.5 | 0.5 |
| C8–C10 Alkyl Sulphate | — | — | 7.0 | — | — | — |
| Benzyl alcohol | — | — | — | 0.8 | 0.8 | 0.8 |
| Amine oxide** | 0.55 | 0.40 | 0.9 | 0.9 | 0.9 | 0.9 |
| Butyl carbitol | 0.55 | 0.55 | — | 0.3 | 0.3 | 0.3 |
| Butoxy propanol | 0.55 | 0.55 | — | 1.2 | 1.2 | 1.2 |
| Ethanol | 9.4 | 9.4 | 2.5 | 1.0 | 1.0 | 1.0 |
| Citric acid | 1.5 | 0.75 | 1.5 | 0.5 | — | 0.7 |
| Water and minors | up to 100% | | | | | |

Poly(ethylene glycol-co-propylene glycol)-mono butyl ether *** used herein has an average molecular weight of 970

| Compositions (weight %) | XIV | XV | XVI | XVII | XVIII | XIX |
|---|---|---|---|---|---|---|
| Hydrogen peroxide | 1.2 | 1.0 | 1.0 | 1.0 | 1.5 | 1.5 |
| Thymol | 0.045 | 0.02 | 0.05 | 0.01 | 0.02 | 0.02 |
| Poly(ethylene glycol) methyl ether**** | 0.25 | 0.25 | 0.5 | 0.5 | 0.5 | 0.5 |
| C8–C10 Alkyl Sulphate | — | — | 7.0 | — | — | — |
| Benzyl alcohol | — | — | — | 0.8 | 0.8 | 0.8 |
| Amine oxide** | 0.55 | 0.40 | 0.9 | 0.9 | 0.9 | 0.9 |
| Butyl carbitol | 0.55 | 0.55 | — | 0.3 | 0.3 | 0.3 |
| Butoxy propanol | 0.55 | 0.55 | — | 1.2 | 1.2 | 1.2 |
| Ethanol | 9.4 | 9.4 | 2.5 | 1.0 | 1.0 | 1.0 |
| Citric acid | 1.5 | 0.75 | 1.5 | 0.5 | — | 0.7 |
| Water and minors | up to 100% | | | | | |

Poly(ethylene glycol) methyl ether**** used herein has an average molecular weight of 750.

| Compositions (weight %) | XX | XXI | XXII | XXIII | XXIV | XXV |
|---|---|---|---|---|---|---|
| Hydrogen peroxide | 1.2 | — | 1.0 | — | 4 | 4 |
| Thymol | — | 0.02 | 0.05 | 0.01 | — | 0.02 |
| Geraniol | — | 0.01 | 0.05 | 0.02 | — | — |
| Poly(ethylene glycol-co-propylene glycol)-mono butyl ether*** | 0.25 | 0.25 | 0.5 | — | — | 0.5 |
| Poly(propylene glycol) mono butyl ether* | 0.25 | — | — | 0.5 | 0.5 | — |
| C8–C10 alkyl Sulphate | — | — | 7.0 | — | — | — |
| Citric acid | 1.5 | 0.75 | 1.5 | 0.5 | — | 0.7 |
| Water and minors | up to 100% | | | | | |

The compositions exemplified above are according to the present invention. They provide excellent immediate and long lasting disinfection when used neat or diluted, e.g. at 1:25 dilution levels, on a hard-surface, while delivering also excellent cleaning performance, especially on greasy stains, and excellent shine properties to the surface treated.

What is claimed is:

1. A liquid disinfecting composition comprising an effective disinfecting amount of a disinfecting material, wherein the disinfectant material comprises a peroxygen bleach, and one or a mixture of poly (alkylene glycol) ethers having the following formula:

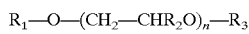

$R_1-O-(CH_2-CHR_2O)_n-R_3$ wherein $R_1$ and $R_2$ are each independently a substituted or unsubstituted, saturated or unsaturated, linear or branched hydrocarbon chain having from 1 to 30 carbon atoms or a hydroxy bearing linear or branched hydrocarbon chain having from 1 to 30 carbon atoms, or $R_2$ is hydrogen, $R_3$ is a substituted or unsubstituted, saturated or unsaturated, linear or branched hydrocarbon chain having from 1 to 30 carbon atoms or a hydroxy bearing linear or branched hydrocarbon chain having from 1 to 30 carbon atoms, and n is greater 2.

2. The composition according to claim 1, wherein $R_1$ and $R_2$ each independently are a substituted or unsubstituted, linear or branched, alkyl group or alkenyl group having from 1 to 16 carbon atoms, or a hydroxy bearing linear or branched alkyl group or alkenyl group having from 1 to 16 care atoms, or $R_2$ is hydrogen, $R_3$ is a substituted or unsubstituted, linear or branched, alkyl group or alkenyl group having from 1 to 16 carbon atoms, or a substituted or unsubstituted, saturated or unsaturated, linear or branched aryl group having 6 to 16 carbon atoms, or a hydroxy bearing linear or branched alkyl group or alkenyl group having from 1 to 16 carbon atoms, and n is from 3 to 2300.

3. The composition according to claim 1 wherein $R_1$ is methyl, $R_2$ is hydrogen or methyl, $R_3$ is butyl, and n is from 3 to 10.

4. The composition according to claim 1 wherein the poly (alkylene glycol) ether or mixture of poly (alkylene glycol) ethers is present at a level of from 0.001% to 10% by weight of the total composition.

5. The composition according to claim 1 wherein the disinfecting material further comprises a component selected from the group consisting of antimicrobial essential oils and actives thereof, quaternary ammonium compounds, paraben, aldehydes, phenolic compounds, alcohols, organic acids, chlorine-type bleaches, and mixtures thereof.

6. The composition according to claim 1 wherein the peroxygen bleach comprises hydrogen peroxide or a water soluble source thereof selected from the group consisting of percarbonates, persilicates, persulphates, perborates, peroxyacids, dialkylperoxides, diacylperoxides, preformed percarboxylic acids, organic and inorganic peroxides, organic and inorganic hydroperoxides, and mixtures thereof.

7. The composition according to claim 1 wherein the composition comprises up to 20% by weight of the total composition of the peroxygen bleach.

8. The composition according to claim 5 wherein the antimicrobial essential oil or an active thereof is selected from the group consisting of thyme oil, lemongrass oil, citrus oil, lemon oil, orange oil, ajowan oil, anise oil, clove oil, aniseed oils cinnamon oil, geranium oil, rose oil, lavender oil, citronella oil, eucalyptus oil, peppermint oil, mint oil, camphor oil, sandalwood oil, cedar oil, rosmarin oil, pine oil, vervaih oil, fleagrass oil, lemongrass oil, ratanhiae oil, thymol, eugenol, menthol, carvacrol, verbenone, eucalyptol, cedrol, anethol, pinocarvone, geraniol, hinokitiol, berberine, ferulic acid, cinnamic acid, methyl salicylic acid, methyl salicylate, terpineol, limonene and mixtures thereof, or a mixture thereof.

9. The composition according to claim 8, wherein the antimicrobial essential oil or active thereof is selected from the group consisting of thyme oil, ajowan oil, citronella oil, olove oil, cinnamon oil, geranium oil, eucalyptol oil, peppermint oil, mint oil, thymol, eugenol, verbenone, eucalyptol, terpineol, cinnamic acid, methyl salicylic acid, limonene, geraniol or a mixture thereof.

10. The composition according to claim 5 wherein the antimicrobial essential oil or active thereof or a mixture thereof is present in the composition at a level up to 20% by weight of the total composition.

11. The composition according to claim 5 wherein said composition further comprises surfactant up to a level of 50% by weight of the total composition.

12. The composition according to claim 11, wherein the surfactant is selected from the group consisting of anionic surfactants, amphoteric surfactants and mixtures thereof.

13. The composition according to claim 11, wherein the surfactant comprises amine oxide surfactant, betaine surfactant, sulfobetaine surfactant, $C_8$–$C_{16}$ alkyl sulfonate, $C_7$–$C_{16}$ alkyl sulfate or $C_7$–$C_{16}$ alkyl alkoxylated sulfate.

14. The composition according to claim 1 which further comprises a component selected from the group consisting of chelants, solvents, pH buffers, builders, stabilisers, bleach activators, soil suspenders, dye transfer agents, brighteners, perfumes, anti dusting agents, enzymes, dispersant, dye transfer inhibitors, pigments, radical scavengers, dyes, and mixtures thereof.

15. The composition according to claim 1, wherein the pH of the composition is not more than 12.

16. The composition according to claim 15, wherein the pH of the composition is between 2 and 9.

17. The composition according to claim 1, wherein the composition is packaged in a spray dispenser.

18. A wipe impregnated with a disinfecting composition according to claim 1.

19. A process of disinfecting a hard-surface with a composition according to claim 1, wherein the process comprises the step of applying the composition before optionally rinsing the hard-surface.

20. The process of disinfecting a hard-surface according to claim 19, wherein the composition is applied in its neat liquid form.

21. The process of disinfecting a hard-surface according to claim 19, wherein the composition is diluted at a dilution level of up to 100 times its weight of water.

22. A liquid disinfecting composition comprising an effective disinfecting amount of a disinfecting material and one or a mixture of poly (alkylene glycol) ethers having the following formula:

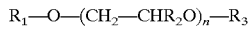

wherein $R_1$ and $R_2$ are each independently a substituted or unsubstituted, saturated or unsaturated, linear or branched hydrocarbon chain having from 1 to 30 carbon atoms or a hydroxy bearing linear or branched hydrocarbon chain having from 1 to 30 carbon atoms or $R_2$ is a hydrogen, $R_3$ is a substituted or unsubstituted, saturated or unsaturated, linear or branched hydrocarbon chain having from 1 to 4 carbon atoms or a hydroxy bearing linear or branched hydrocarbon chain having from 1 to 4 carbon atoms, and n is greater than 2.

23. The composition according to disinfecting material comprises a peroxygen bleach, and 0.001% to 10%, by weight of the total composition, of a component selected from the group consisting of poly (propylene glycol) mono butyl eter, poly(ethylene glycol-co-propylene glycol) mono butyl other, poly (ethylene glycol) dimethyl ether, poly (ethylene glycol-co-propylene glycol) dimethyl ether, poly (ethylene glycol) stearate and mixtures thereof.

24. A liquid disinfecting composition comprising an effective disinfecting amount of a disinfecting material, wherein the disinfecting material comprises a peroxygen bleach, and one or a mixture of poly (alkylene glycol) ethers having the following formula:

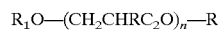

wherein $R_1$ and $R_2$ are each independently a substituted or unsubstituted, saturated or unsaturated, linear or branched hydrocarbon chain having from 1 to 30 carbon atoms or a hydroxy bearing linear or branched hydrocarbon chain having from 1 to 30 carbon atoms or $R_2$ is a hydrogen, $R_3$ is a substituted or unsubstituted, saturated or unsaturated, linear or branched hydrocarbon chain having from 1 to 4 carbon atoms or a hydroxy bearing linear or branched hydrocarbon chain having from 1 to 4 carbon atoms, and n is greater than 2.

* * * * *